United States Patent [19]

Kakutani et al.

[11] Patent Number: 4,970,161

[45] Date of Patent: Nov. 13, 1990

[54] HUMAN INTERFERON-GAMMA

[75] Inventors: Tetsu Kakutani, Kakogawa; Keiji Matsumoto, Nishinomiya; Hiroyuki Maruyama; Kaku Nakagawa, both of Kakogawa; Shinichi Yokota; Hideo Niwa, both of Ibaraki; Katsuhiro Shinjo, Kobe; Hajime Kawaharada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 144,988

[22] Filed: Jan. 19, 1988

Related U.S. Application Data

[63] Continuation-in-part of Ser. No. 740,773, Jun. 3, 1985, abandoned.

[30] Foreign Application Priority Data

Jun. 11, 1984 [JP] Japan ................................ 59-11648
Apr. 27, 1985 [JP] Japan ................................ 60-91618
Apr. 27, 1985 [JP] Japan ................................ 60-91619

[51] Int. Cl.$^5$ .................. C12N 15/00; C12N 5/00; C12P 21/00
[52] U.S. Cl. .................. 435/240.2; 435/172.3; 435/69.51; 435/317.1; 435/320; 935/22; 935/23; 935/34
[58] Field of Search ................ 435/172.3, 68, 70, 240, 435/253, 320, 69.51, 172.3, 240.2, 320, 317.1; 935/34

[56] References Cited

FOREIGN PATENT DOCUMENTS 0063482 4/1982 European Pat. Off. .
0077670 10/1982 European Pat. Off. .
0159714 10/1985 European Pat. Off. .
60-202899 10/1985 Japan .

OTHER PUBLICATIONS

Lewin, Genes, John Wiley & Sons Pub., pp. 186-192, (1983).
Phil. Trans. R. Soc. Land. B 299, 29 (1982), Fiers et al.
Proc. Natl. Acad. Sci. USA, vol. 81, pp. 5086-5090, Aug. 1984, Fukunaga et al.
Proc. Natl. Acad. Sci. USA, vol. 79, pp. 7857-7861, Dec. 1982, Le et al.
Genetic Engineering, vol. 2, Sellow et al. ed. Plenum, New York, 83-101, (1980), Hamer.
The EMBO Journal, vol. No. 8, pp. 953-958, 1982, Taya et al., European Search Report.

Primary Examiner—Charles F. Warren
Assistant Examiner—Jasemine C. Chambers
Attorney, Agent, or Firm—Armstrong, Nikadio, Marmelstein, Kubovcik & Murray

[57] ABSTRACT

A DNA sequence on which a chromosomal DNA sequence coding for human interferon-γ (HuIFN-γ) and having a TATA box is ligated to a sequence of a promoter. Cell cultures transformed with said DNA revealed a higher expression of HuIFN- than cell cultures transformed with a DNA which does not have such TATA box. When transformed with said DNA, cell cultures produced HuIFN-γ in a serum free medium. Transformed cell cultures derived from blood cells of HuIFN-γ resistant human cell-line also could produce HuIFN-γ.

4 Claims, 9 Drawing Sheets

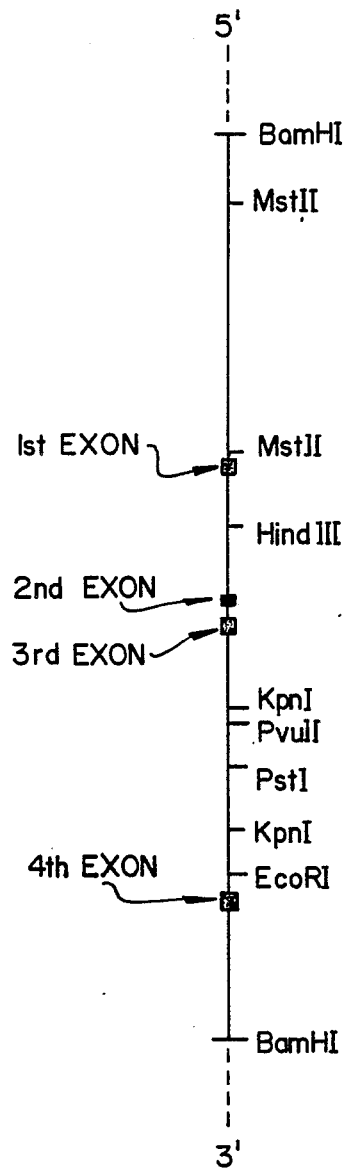
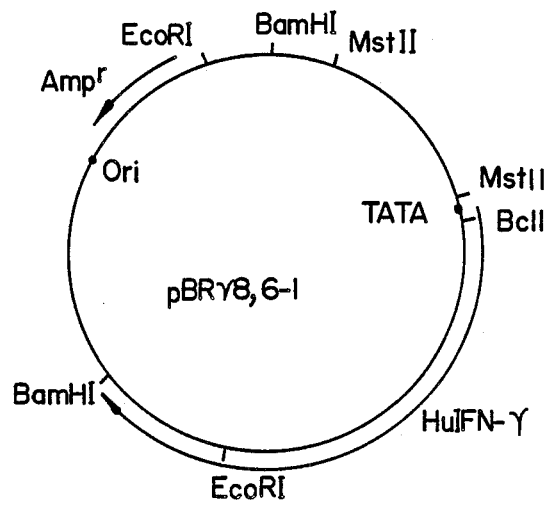
FIG. 2
FIG. 1

HUMAN INTERFERON-GAMMA

This application is a continuation-in-part of application Ser. No. 740,773, filed June 3, 1985.

FIELD OF THE INVENTION

The present invention relates to a DNA sequence including a chromosomal DNA sequence coding for human interferon-γ (hereinafter referred to as HuINF-γ) which enables HuIFN-γ to be expressed in high yields in animal cell cultures, to cell cultures transformed with said DNA sequence, and, in addition, to a method for producing HuIFN-γ by cultivating said transformed cell cultures and recovering HuIFN-γ.

HuIFN-γ is a glycoprotein having antivirus activity, antitumor activity and immunoregulating activity, and therefore is expected to be a therapeutic agent for various diseases.

BACKGROUND OF THE INVENTION

(Interferon)

Interferon (hereinafter referred to as IFN) was, at first, discovered as a virus-inhibiting substance, but thereafter was shown to be a substance that bears varied biological and immunological activities. From fairly long ago, IFN was known to be effective in inhibiting cell proliferation [Rubin, B. Y. et al. (1980): Proc. Natl. Acad. Sci. U.S.A, 77, 5928]. Further, with the recent advance of immunological science, it has come revealed that IFN can activate natural killer cells and other cells having antibody-dependent cell cytotoxicity which are supposed to take part in what is called immunological surveillance mechanism of cancer, so as to enhance the antitumor activity of those cells [Catalona, W. J. et al. (1981): Nature, 291, 77]. It has also been shown that IFN enhances the activity of cytotoxic T-cell [Lindahl, P. et al. (1972): Proc. Natl. Acad. Sci., 69, 721], and activates macrophages to change them to ones with antitumor actions [Le, J. et al. (1983): J. Immunol., 131, 2821]. These findings indicate the possibilities of IFN as an antitumor agent.

According to differences in physiological, biochemical and immunological properties of proteins, or in producing cells and inducing methods, HuIFNs are classified into three groups, which are called IFN-α, IFN-β, and IFN-γ, respectively [Stewart II, W. E. et al. (1980): Nature, 286, 110].

Among others, IFN-γ has an ability to inhibit cell proliferation at much lower concentrations comparing with IFN-α, and IFN-γ [Rubin, B. Y. et al. (1980): Proc Natl. Acad. Sci. U.S.A., 77, 5928], and also to activate cells, including natural killer cell, killer T-cell, K-cell and macrophage, which act on the basis of what is called immunological surveillance mechanism of cancer. Great expectations therefore are held by clinical application for IFN-γ.

HuIFN-γ is found to have molecular weight of 20,000 or 25,000 [Yip, Y. K. et al. (1982) Proc. Natl. Acad. Sci. U.S.A., 79. 1820]. HuIFN-γ is a glycoprotein having 143 amino acids and only one gene coding for HuIFN-γ is known [Gray, P. W. et al. (1982): Nature, 295, 503].

HuIFN-γ is known to be induced with human lymphocytes stimulated by phytohemaagglutinin, staphylococcal enterotoxin A, concanavalin A, or galactose oxidase [Wheelock, E. F. (1965): Science, 149, 310; Langford, M. P. et al. (1979): Infect Immun , 26, 36; de Lay, M. et al. (1980): Eur. J. Immunol., 10, 877; Dianzani, F. et al. (1979): Infect. Immun., 25, 879]. Nevertheless, since these producing methods necessitate consumption of large amounts of fresh human lymphocytes, mass-production of HuIFN-γ as a therapeutic drug by such means is made difficult. Recently the realization of cloning of cDNA has made the production of HuIFN-γ-like protein by *Escherichia coli* possible [Gray, P. W. et al (1982): Nature, 295, 503]. However, since the mechanisms of protein synthesis in animal cells are different from those of microorganisms, IFN-γ produced by microorganisms are often different from those naturally produced with respect to the amino terminus of protein. Furthermore, IFN-γ produced by microorganisms has no combined sugar chains, while the natural HuIFN-γ has them. In such manners IFN-γ produced by microbial protein synthesis system is substantially different from the natural HuIFN-γ, and therefore, in cases of prolonged or frequent use of such IFN-γ, such problems as reduction of activities of the drug by antigen-antibody reaction and allergic responses such as shock reactions remain under apprehension. According to Le et al., IFN-γ produced in *Escherichia coli* is different from natural HuIFN-γ in reactivity of antigen-antibody reaction with monoclonal antibodies, and the difference of reactivity is not due to the absence of sugar chain [Le et al. (1984): J. Immunol., 132, 1300]. While, on the other hand, it was reported that HuIFN-γ was also produced by cloned T-cell line [Nathan, H. et al. (1981): Nature, 292, 842], T-cell hybridoma [Le et al. (1982): Proc. Natl. Acad. Sci. U.S.A., 79, 7857], and T-cell which was transformed by adult T-cell leukemia virus [Sugamura, K. et al. (1983): J. Immunol., 131, 1611]. These cells are believed to contain human leukemia virus as provirus, or to release virus particles out of themselves, and are therefore still problematical with respect to potential biohazards [Sugamura, K. et al. (1983): ibid.].

(Production of HuIFN-γ by Using Animal Cell Cultures)

On the other hand, production of HuIFN-γ was also attempted with the use of animal cell cultures in which simian virus 40 (hereinafter referred to as SV40) promoter sequence had been ligated to the DNA sequence [Gray, P. W. et al. (1982): Nature, 295, 503; Haynes, J. et al. (1983): Nucleic Acids Res., 11, 687; Scahill, S. J. et al. (1983): Proc. Natl. Acad. Sci. U.S.A., 80, 4654; Devos, R. et al. (1982): Nucleic Acids Res., 10, 2487' European Patent Laid Open No. 77670 and No. 88540]. But DNA used in these producing methods was cDNA.

It has been known that many of the proteins of higher organisms are coded on chromosomal DNA sequences in the form of some interrupted sequences. The DNA sequences which code matured messenger RNA are celled exons, and the intervening sequences are introns. Although it is still unclear what the biological significance and function of intron are, it has been known that ovalbumin [Wickens, M. P. et al. (1980): Nature, 285, 628], or viral protein [Lai, C. J. et al. (1979): Proc. Natl. Acad. Sci. U.S.A., 76, 71] production in animal cell cultures, into which an intron-deleted ovalbumin gene or viral gene was introduced, was very much less active than in the cases of intron-containing sequences. Further, it has also been known that the addition of introns of -globin gene to intron-deleted SV40 gene leads to accumulation of stable messenger RNA (hereinafter referred to as mRNA) [Homer, D. H. et al. (1979): Cell, 18, 1299].

Removing the sequence of intron out of primary RNA transcribed from gene is called splicing. Splicing is supposed to be necessary for the accumulation of stable mRNA or the transfer of mRNA from nucleus to cytoplasm. Therefore, in some of the above producing methods using HuIFN-γ intron-free cDNA, it is supposed that the addition of viral introns to the cDNA sequence of HuIFN-γ makes the accumulation of mRNA in cells possible. As shown in FIG. 1, the HuIFN-γ chromosomal DNA is composed of four exons, three introns, and two sequences adjacent to the 5'-side and the 3'-side (Gray, P. W. et al. (1982): Nature, 298, 859; Taya, Y. et al. (1982): EMBO J., 1, 953].

An example for producing HuIFN-γ by animal cell cultures transformed with chromosomal DNA which is ligated to SV40 early promoter is known [European Patent Application Laid Open No. 159714 (1985)]. But "TATA box" sequence, which determines the position from which mRNA is transcribed, used in the HuIFN-γ expression vector of the above-mentioned cDNA or genomic DNA is derived from SV40, and the amount of HuIFN-γ produced by the animal cell culture transformed with the vector is of a low- level.

The SV40 promoter region is contained in a 350 base pair (bp) PvuII-HindIII fragment and in this promoter region there is 72 bp repeats called enhancer. (hereinafter the promoter region is sometimes referred to as promoter/enhancer sequence.)

The inventors of the present invention have prepared various HuIFN-γ expression vectors to compare their HuIFN-γ expressing activity and found, which has led to this invention, that HuIFN-γ is expressed in high yield only when HuIFN-γ chromosomal DNA sequence having TATA box is ligated to a promoter region such as SV40 promoter region (i.e. promoter/enhancer sequence).

HuIFN-γ is a glycoprotein. The structure of the sugar chain of HuIFN-γ is still unclear in many respects. For example, it is unknown whether there are differences between sugar chains of HuIFN-γ produced by cells of organisms other than human and HuIFN-γ produced in human cells in their structure and antigenic properties. The HuIFN-γ produced by cells derived from human is, however, thought to be the same as the natural one, and to be safer to use than those produced by cells of organisms other than human. Furthermore, while the latter are suspected to cause problems such as allergic and shock reactions during their long-term therapeutic administration because of possible contamination of their preparations with components such as foreign protein or the like or secretions from the parent organisms, preparations from the former never contain substantial amount of any substance other than naturally occurring human components, that is, substances intrinsically existing in the human blood. For these reasons, a greater degree of safety is expected for products from cells derived from humans.

For making cell cultures derived from human cells for producing HuIFN-γ, transformation of human cells by a HuIFN-γ expression vector may be practical. However, since such transformed human cells are killed off by self-produced HuIFN-65 which are generally highly toxic to cells derived from human, it is believed to be extremely difficult to acquire a transformed strain which can be subcultured. Thus, whereas a transformed strain which is subculturable to produce HuIFN-γ can be easily obtained with hamster cells, a transformed strain which is subculturable is difficult to obtain from cell cultures derived from human.

Most cells in culture have a tendency to stick to vessel walls. Even if cultured under mechanical agitation of the culture medium, cells having such a tendency do not proliferate to separate off-springs, but yield cell flocuations. Such flocuations are uneven in size, and result in an uneven cell density in the culture medium. In addition, because of difficulty in controlling the agitating conditions when the agitation is mild, cells exhibit a greater tendency to stick. When the agitation is too strong, it is liable to damage cells.

BRIEF SUMMARY OF THE INVENTION

Based on the above background, the inventors isolated chromosomal DNA coding for HuIFN-γ, and prepared plasmids in which the HuIFN-γ chromosomal DNA having its TATA box is ligated to a promoter sequence, for example, SV40 early promoter of SV40 late promoter. Further, these plasmids were prepared to contain a selective marker gene, for example, Ecogpt. The plasmids thus constructed such as pSVeSmaIγ, pSV2LγT or pSV3LγT, were introduced into varied animal cells using the calcium phosphate method, the cell fusion method, and other known method to obtain transformed cell lines. Furthermore, the inventors obtained subculturable transformed cell lines for the first time by using HuIFN-γ-resistant cell cultures derived from human, HuIFN-γ-resistant mutants. It is thought that, basically, subculturable HuIFN-γ-producing cell lines can be derived from any sort of cell cultures derived from human cells, and that, consequently, can produce natural-type HuIFN-γ in extremely high yields with safety.

In addition, the inventors succeeded in separating HuIFN-γ producing strains through transformation of cell lines derived from blood cells which are proliferable as separate cells that, during cultivation, do not substantially stick to vessel walls, and yield few cell flocuations. These HuIFN-γ-producing cell lines can be very readily submitted to suspension culture process to conduct large scale culture easily. The present invention is regarded as important in providing for a means to supply highly safe HuIFN-γ on a large scale.

BRIEF DESCRIPTION OF THE DRAWINGS

FIG. 1 displays a restriction map of the 8.6 Kb BamHI fragment which contains HuIFN-γ gene.

FIG. 2 is a pictorial representation of pBRγ8.6-1.

DETAILED DESCRIPTION (Chromosomal DNA)

Figure 3:
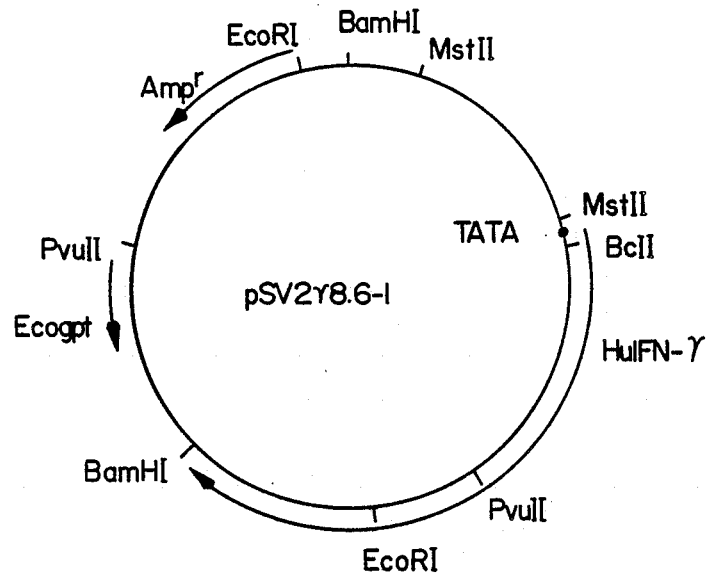
FIG. 3 is a pictorial representation of pSV2γ8.6-1 and pSV2γ8.6-2.
Figure 3:
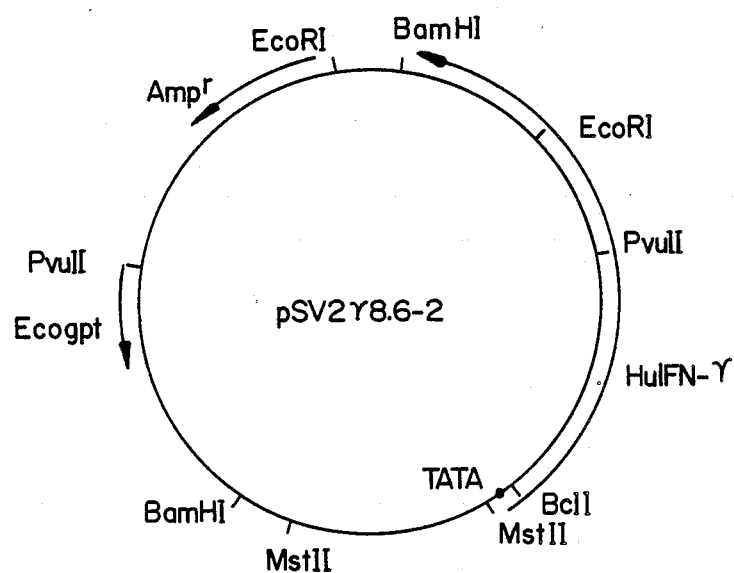

Chromosomal DNA sequence which codes for HuIFN-γ is cloned from human DNA. The human DNA is prepared by the method of Blin, et al [Blin, N. et al. (1976): Nucleic Acids. Res., 3, 2303] from human leukocytes or tissues, for example. As a vector for cloning of HuIFN-γ gene, phage vectors represented by Charon 28, plasmid vectors represented by pBR322, or cosmids represented by pHC79 are used. However, the gene manipulation technique is generally adopted with the use of phage vector which can clone long-chain DNA fragments with high efficiencies. After cutting of human high-molecular DNA by an appropriate restriction enzyme, the DNA fragment is inserted in place of the substitutable region of phage DNA to make the recombinant phage DNA. Next, using the in vitro packaging technique, infectious phage particles are prepared. The phage particles are plated together with host Escherichia coli to make plaques of recombinant phages [Enquist, L. et al. (1979): Methods in Enzymology, 68, 281; Horn, B. (1979): Methods in Enzymology, 68, 299]. For detection of the plaques of the recombinant phage which has DNA fragments coding for HuIFN-γ, the plaque hybridization technique is applicable using 32P-labelled cDNA or synthetic DNA as a probe [Woo, S. L. C. (1979): Methods in Enzymology, 68, 389; Szostak, J. W. et al. (1979): Methods in Enzymology, 68, 419]. Furthermore, the recombinant phage which has HuIFN-γ gene can be prepared to a large amount by recovering from a plaque selected by the plaque hybridization, and by culturing together with host Escherichia coli. The recombinant phage DNA can be prepared according to the method described [Maniatis, T. et al (1982): Molecular Cloning a Laboratory Mannual, Cold Spring Harbor Laboratory].

When human chromosomal DNA is cleaved by restriction enzyme BamHI, the gene region which codes HuIFN-γ is contained within the DNA fragment of about 8.6 Kb, as shown in FIG. 1, and the DNA sequence of the 5'-region of HuIFN-γ chromosomal DNA is as follows:

TABLE 1

DNA sequence of the 5'-region of HuIFn-γ chromosomal DNA sequence

| | | | | | |
|---|---|---|---|---|---|
| AGCAAATGAT | CAATGTGCTT | TGTGAATGAA | GAGTCAACAT | TTTACCAGGG | 50 |
| CGAAGTGGGG | AGGTACAAAA | AAATTTCCAG | TCCTTGAATG | GTGTGAAGTA | 100 |
| AAAGTGCCTC | AAAGAATCCC | ACCAGAATGG | CACAGGTGGG | CATAATGGGT | 150 |
| CTGTCTCATC | GTCAAAGGAC | CCAAGGAGTC | TAAAGGAAAC | TCTAACTACA | 200 |
| ACACCCAAAT | GCCACAAAAC | CTTAGTTATT | AATACAAACT | ATCATCCCTG | 250 |
| CCTATCTGTC | ACCATCTCAT | CTTAAAAAAC | TTGTGAAAAT | ACGTAAT<u>CCT</u> | 300 |
| <u>CAGGAGACTT</u> | CAATTAGG<u>TA</u> | <u>TAAATAC</u>CAG | CAGCCAGAGG | AGGTGCAGCA | 350 |

MstII                      TATA box                                      1st exon →

| | | | | | |
|---|---|---|---|---|---|
| CATTGTTCTG | ATCATCTGAA | GATCAGCTAT | TAGAAGAGAA | AGATCAGTTA | 400 |
| AGTCCTTTGG | ACCTGATCAG | CTTGATACAA | GAACTACTGA | TTTCAACTTC | 450 |

BclI

| | | | | | |
|---|---|---|---|---|---|
| TTTGGCTTAA | TTCTCTCGGA | AACGATGAAA | TATACAAGTT | ATATCTTGGC | 500 |

→ Protein synthesis

| | | | | | |
|---|---|---|---|---|---|
| TTTTCAGCTC | TGCATCGTTT | TGGGTTVTVT | TGGCTGTTAC | TGCCAGGACC | 550 |
| CATATGTAAA | AGAAGCAGAA | AACCTTAAGA | AATATTTTGT | AAGTATGACT | 600 |
| TTTTAATAGT | ACTTGTTTGT | GGTTGAAAAT | GACTGAATAT | CGACTTGCTG | 650 |
| TAGCATCTCT | GATAGGCTGT | CATCTCTTGT | AGGCAGTCAT | TTTGAGATTT | 700 |

TATA box is thought to exist near 320, and transcription would start from near 350, followed by the first exon (from 347) and HuIFN-γ protein is synthesized from ATG at 475.

To use the TATA box of HuIFN-γ, it is preferable to cut HuIFN-γ chromosomal DNA sequence with a restriction enzyme MstII at 298 and ligate the sequence including the TATA box to a promoter sequence.

(Promoters)

The promoter region refers to a sequence of promoter region which contains the initiation origin of mRNA synthesis, but not the methionine codon which is the first amino acid of the protein that is regulated by the said promoter.

As suitable promoter sequences to which HuIFN-γ chromosomal DNA sequence having its TATA box is ligated, promotors such, for example, as a SV40 early promoter, a SV40 late promoter, a thymidine kinase promoter type 1 of herpes simplex virus can be used.

SV40 early promoter is contained in an about 350 bp HindIII-PvuIII fragment, as mentioned above, and its DNA sequence is as follows:

TABLE 2

DNA sequence of SV40 HindIII-PvuII fragment.

```
1                       25                        50
CAGCTGTGGAATGTGTGTCAGTTAGGGTGTGGAAAGTCCCCAGGCTCCCC
51                      75                       100
AGCAGGCAGAAGTATGCAAAGCATGCATCTCAATTAGTCAGCAACCAGGT
101                    125                       150
GTGGAAAGTCCCCAGGCTCCCCAGcAGGCAGAAGTATGCAAAGCATGCAT
151                    175                       200
CTCAATTAGTCAGCAACCATAGTCCCGCCCCTAACTCCGCCCATCCCGCC
201                    225                       250
CCTAACTCCGCCCAGTTCCGCCCATTCTCCGCCCCATGGCTGACTAATTT
```

TABLE 2-continued

DNA sequence of SV40 HindIII-PvuII fragment.

```
251                       275                       300
TTTTTATTTATGCAGAGGCCGAGGCCGCCTCGGCCTCTGAGCTATTCCAG
    TATA                      mRNA
301                       325                       350
AAGTAGTGAGGAGGCTTTTTTGGAGGCCTAGGCTTTTGCAAAAAGCTTTG
                                            HindIII
351
CAAAGATGGATATAAAGTT
    ——>
    T-antigen
```

Transcriptional origin exists near 280 and TATA box at 255–261. Codon ATG for the first amino acid (methionine) of T-antigen is at 356 (underlined). In this region, there are 72 bp repeats which activate a transcription called enhancer and, therefore, if a gene having its transcriptional activity is near this region, the gene is activated in its transcriptional activity.

Furthermore, SV40 promoter/enhancer region has a late promoter activity in a direction opposite to the early promoter. The late promoter does not seem to have a TATA box, and late mRNA seems to be synthesized from various points.

(Plasmid)

To obtain an expression vector used in this invention, for example, SV40 DNA which is cut at a PvuII site of 1 (Table 2) or at a HindIII site of 343 (Table 2) is ligated to a chromosomal DNA sequence of MstII-BamHI fragment with a suitable linker. pSVeSmaIγ is an example of a vector which has a HuIFN-γ chromosomal DNA sequence having its TATA box ligated to HindIII site of SV40 promoter.

For the purpose of selective proliferation of the only cells where the desired genes are introduced and stably expressed, such a DNA sequence which also possesses both a sequence in which a HuIFN-γ chromosomal DNA sequence having TATA box is ligated to a promoter sequence, and a selective marker gene, is appropriate. As the selective marker in animal cells, such genes as Ecogpt [Mulligan, R. C. et al. (1980): Science, 209, 1422), neo (Southern, P. J. et al. (1982): J. Mol. Appl. Genet., 1, 327], , and dhfr [Wigler, M. et al. (1980): Proc. Natl. Acad. Sci. U.S.A., 77, 3567] are used.

For the purpose of preparing a large amount of HuIFN-γ expression vector, it is desirable that such a DNA is plasmid or phage DNA which can be replicated in *Escherichia coli*, and be preparable on a large scale. Plasmid pSVeSmaIγ, pSV2LγT or pSV3LγT which is described in examples 4, 8 and 9 meet the above purpose. In other words, all these plasmids are characterized in that the DNA sequence possesses the DNA replication origin (ori) of the *Escherichia coli* and of the animal cell cultures, the HuIFN-γ chromosomal DNA sequence having its TATA box ligated to a promoter and selective marker genes in *Escherichia coli* (Ampicillin resistant gene) and in animal cell cultures (Ecogpt).

(Transfection)

As for means for introducing DNA into animal cell cultures, such methods as the calcium phosphate method [Wigler, M. et al. (1977): Cell, 11, 223], microinjection method [Anderson, W. F. et al. (1980): Proc. Natl. Acad. Sci. U.S.A., 77, 5399], liposome method, DEAE-dextran method or cell fusion method [Schoffner, W. et al. (1980): Proc. Natl. Acad. Sci. U.S.A., 77, 2163], are used, although these methods differ from one another in transfection efficiency. As DNA materials for the calcium phosphate method, such microorganisms as *Escherichia coli* as well as phage and the like are applicable besides DNA solutions. In the cell fusion method, microbial protoplasts which hold the desired DNA sequence as a plasmid is used.

The mRNA synthesis from SV40 late promoter has been known to be increased in the presence of SV40 T antigen [Keller, J. M. et al. (1984): Cell, 36, 381]. It was found that the yield of HuIFN-γ was enhanced if cells were co-transfected with DNA sequence which codes SV 40 T antigen, concurrently with the introduction of HuIFN-γ gene which contained SV40 late promoter. When cells are co-transfected with DNA sequence coding for SV40 T antigen, T antigen bearing plasmid such as pSV3gpt can be used. Further, when cells are transfected with a DNA sequence which has both HuIFN-γ gene and T antigen gene on itself, both the HuIFN-γ and the T antigen gene are integrated into the cells more effectively than by co-transfection of them. It may also be possible to obtain highly HuIFN-γ-expressing cell lines using various cell strains. Furthermore, it is also possible to use a SV40 transformant as a host.

(Cell Cultures)

Cell cultures used in this invention are available from American Type Culture Collection (ATCC), which are cells derived from hamster, monkey, mouse, rat or human, including CHO (hamster ovary cells), HeLa (human cerevicitis tumor cells), FL (human amnion cells), WISH (human amnion cells), WI-26VA4 (human lung cells transformed by SV40), and Vero (kidney cells of African green monkey). It is possible to obtain the production of HuIFN-γ active in cultured cells, hybridomas, normal and variant cells at least derived from vertebrates, and cells transformed by virus, provided that the production methods described in this specification are employed. Further, improvement in safety of products from the cell line transformed by SV40 is expected in comparison with cell lines with an unaccountable malignancy provided that proper means are taken. As a transformant by SV40, WI-26 VA4 is known.

For selecting HuIFN-γ-resistant cell lines or HuIFN-γ-resistant variants out of many cell cultures derived from human, subcultivation of culture cells in a medium containing HuIFN-γ by one unit to several ten thousand units is useful. Whereas HuIFN-γ-sensitive culture cells derived from human are denatured, deformed, and finally killed off by the toxicity of HuIFN-γ during the subcultivation, the HuIFN-γ-resistant cell lines never are affected, but continue to grow. The latter therefore are selected out easily. In addition, HuIFN-γ-sensitive lines turn significantly sensitive to a double-stranded RNA, poly I:C, when being treated with HuIFN-γ, and the cells are therefore denatured markedly and killed when being cultured in a medium containing poly I:C. Thus the HuIFN-γ-resistant cell lines are distinguished from these HuIFN-γ-sensitive cell lines.

Established cell lines derived from blood cells refer to, for mammals, such cells as lymphoblasts, myeloblasts, monocytes and erythroblasts which are derived from their stem cells, respectively, and, in addition, to cell lines established from cells which are further differentiated or derived from the said blastocytes. The established cells derived from blood cells which have been proliferated in a common medium, are round morphologically, and suitable for suspension culture. In addition, the use of such established cells producing globulin as hosts is advantageous to production of HuIFN-γ, because they are regarded as having high abilities to synthesize and secrete proteins.

The inventors made trial of varied animal cell cultures derived from blood cells, which were obtained from the ATCC, including MOPC-31C (plastocytoma, MPC 11 (myeloma), MB III (lymphosarcoma), RBL-1 (leakemic basophilic granulocyte), RPMI 7666 (lymphoblastoid), MOLT-3 (acute lymphoblastic leukemia), L1210, CCRF-CEM, or EL4, U937, and X63-Ag8.653. They can produce HuIFN-γ active in established cells, hybridomas, normal and variant cells at least derived from mammalian blood cells, and cells transformed by virus, provided that the production methods described in this specification are employed.

(Production and Purification of HuIFN-γ)

It has been found that cells which were made to produce HuIFN-γ by the introduction of HuIFN-γ chromosomal DAN sequence having TATA box which is ligated to a promoter by, for example, the calcium phosphate method, can produce HuIFN-γ not only in a medium containing serum, but also in a serum-free medium. The use of a serum-free medium for production of HuIFN-γ makes the recovery and purification of HuIFN-γ from medium easier.

Known methods are applicable for the recovery and purification of HuIFN-γ from medium. For example, HuIFN-γ can be recovered according to the procedures that HuIFN-γ is adsorbed by a controlled pore glass (Electronucleonics Corp.), washed with PBS (0.15M NaCl-0.15M phosphoric acid buffer; pH=7.4), eluted with PBS containing polyethylene glycol by 50%, again adsorbed by ConA-Sepharose, eluted with phosphoric acid buffer containing 0.15M NaCl and 0.15Mα-methyl-D-mannoside, and chromatographed on Biogel-P-100.

(Determination of Activity of IFN)

The activity of HuIFN-γ was determined with the CPE-inhibiting method with the combined use of FL cell and vascular stomatitis virus or sindovis virus [Philip, c. et al. (1981): Methods in Enzymology, 78, 387].

(Summary)

As shown in examples, cells transformed with DNA sequences (such as pSVeSmaIγ, pSV2LγT, pSV3LγT and other plasmids) in which a chromosomal DNA sequence having TATA box is ligated to a SV40 promoter/enhancer sequence revealed an extremely high level of expression of HuIFN-γ, whereas cells transformed with DNA sequences not having a TATA box of a HuIFN-γ chromosomal DNA (pSVeBaIIγ, pSV2Lγ and other plasmids) did reveal only a low expression level. The reasons seem to be 1. in HuIFN-γ chromosomal DNA sequence having TATA box mRNA formed is believed to be the same as natural mRNA of HuIFN-γ and the stability of the mRNA therefore seems to be high, 2. chromosomal DNA sequence having TATA box has in itself a promoter activity, which is efficiently activated by SV40 72 bp repeats, and 3. TATA box itself has a promoter activity and transcriptional activity would therefore be enhanced synergetically by SV40 promoter/enhancer. In any case, there exists, no doubt, a clear difference between the HuIFN-γ production method using chromosomal DNA sequence having TATA box and the one using chromosomal DNA sequence not having TATA box.

EXAMPLES

Various experiments which were relevant to the invention and described in the Examples given below, were carried out in accordance with "the Japanese guideline on Recombinant DNA" prescribed by the Prime Minister. Detailed manipulations of phages, plasmids, DNA, various enzymes and *Escherichia coli* in Examples were performed by reference to the following journals or books:

1. Proteins, Nucleic Acids and Enzymes, Vol. 26, No. 4 (Extra Edition: Gene Manipulation) (1981). Kyoritsu Publishing Co.

2. Y. Takagi: Experimental Methods of Gene Manipulation, 1981. Kodansha Ltd.

3. Y. Takagi: Manual of Gene Manipulation, 1982. Kodansha Ltd.

4. T. Maniatis et al.: Molecular Cloning a Laboratory manual, 1982. Cold Spring Harbor Laboratory 5. L. Grossman et al.: Methods in Enzymology, Vol. 65, 1980. Academic Press 6. R. Wu: Methods in Enzymology, Vol. 68, 1979. Academic Press

EXAMPLE 1

Cloning of HuIFN-γ gene

Blood samples were taken out of a plural number of healthy adults, and, after collecting the buffy coat, hemolysed by adding about ten-fold volume of 0.83% NH$_4$Cl. The sample was washed with an Eagle's MEM medium to obtain leucocytes. Ten billion ($10^{10}$) leucocytes were shaken with 50 ml of a solution containing 0.5M EDTA, 0.51 sarcosyl, and 100 μg/ml protease K for 3 hours at 50° C. to be dissolved. The obtained solution was extracted with phenyl three times, and the aqueous layer was dialysed against 20 mM tris.HCl (pH 8.0), 10 mM EDTA, and 10 mM NaCl. The dialyzate was treated with 100 μg/ml ribonuclease for 3.5 hours at 37° C., again extracted with phenol, and dialysed against 20 mM tris.HCl (pH 8.0), 1 mM EDTA, and 10 mM NaCl to obtain about 33 mg of high molecular human DNA. The human DNA was digested with a restriction enzyme BamHI, and then BamHI DNA fragments of about 8 to 9 kilobases (hereinafter abbreviated as kb) were prepared with sucrose density-gradient centrifugation. Lambda (λ)-phage vector Charon 28

DNA was digested with BamHI, and the fractions containing the left-arm and right-arm of Charon 28 were collected with sucrose density-gradient centrifugation, and recovered by ethanol precipitation. The DNA fragments with both arms of Charon 28 and the human BamHI fragments of 8 to 9 kb were ligated together using T4 DNA ligase. Then, the ligated DNA was submitted to an in vitro packaging technique according to the Enquist-Sternberg method [Enquist, L. and N. Sternberg (1979): Methods in Enzymol., 28, 281] to from plaques of recombinant phages with the use of *Escherichia coli* LE392 as a host. Next, HuIFN-γ gene-bearing recombinant phage clones were selected out according to the plaque hybridization technique [Benton, W. D. and R. W. Davis (1977): Science, 196, 180]. Oligonucleotides CTTGGCTGTTAC, CCTGGCAG-TAAC, AND GCTCTTCGACCTCG were synthesized by the phosphotriester method [Miyoshi, K. et al. (1980): Nucleic Acids Res., 8, 5507], labelled with (γ-$^{32}$p) ATP and T4 polynucleotide kinase, and used as probes.

Four phage clones, S8-11 S18-6, S19-5 ahd S20-1 which hybridized with all of three synthetic DNA probes were obtained out of about two million recombinant phages. DNA was prepared from the respective phage cloned, and digested with the restriction enzyme BamHI. As a result, a DNA fragment of about 8.6 kb proved to be contained in each phage clone. Furthermore, by the restriction enzyme analysis, and the analysis of DNA sequences mentioned later, the selected four recombinant phage clones were identified as those containing HuIFN-γ BamHI fragments of 8.6 kb.

EXAMPLE 2

Preparation of pBRγ8.6-1, pSV2γ8.6-1 and pSV2γ8.6-2 DNA of phage clone S8-11 containing HuIFN-γ gene was degested with the restriction enzyme BamHI, and ligated to a BamHI site of a plasmid pBR322 which had been treated with bacterial alkaline phosphatase [Bolivar, F. et al. (1977): Gene, 2, 95] and *Escherichia coli* C600 γ$^-$m$^-$ was transformed with this modified plasmid. A transformant which had a plasmid where HuIFN-γ gene of about 8.6 kb had been inserted into BamHI site of pBR322 and which had been selected out as ampicillin-resistant and tetracycline-sensitive, was designated as pBRγ8.6-1. The structure of pBRγ8.6-1 is shown in FIG. 2.

The plasmid pBRγ8.6-1 was digested with BamHI, a DNA fragment of about 8.6 kb was prepared by agarose gel electrophoresis and ligated to the plasmid pSV2gpt which had been treated with bacterial alkaline phosphatase with the use of T4 DNA ligase and *Escherichia coli* C600γ$^-$m$^-$ was transformed with this modified plasmid. Strains bearing plasmids pSV2γ8.6-1 and pSV2γ8.6-2, whose structure are shown in FIG. 3, were selected from among transformants.

Plasmids pSV2γ8.6-1 and pSV2γ8.6-2 are plasmids where HuIFN-γ gene-bearing DNA fragment has been inserted clockwise and counterclockwise into the BamHI sites of pSV2gpt, respectively. The respective plasmid DNA was prepared by cesium chloride density-equilibrium centrifugation. The plasmid DNA was prepared as needed with the use of *Escherichia coli* GM33 dam$^-$ as a host.

EXAMPLE 3

DNA sequence of 5'-side of HuIFN-γ chromosomal DNA

The DNA sequence of THE HuIFN-γ gene of plasmid pBRγ8.6-1 was determined according to the Maxam-Gilbert method [Maxam, A. M. and W. Gilber (1980): Methods in Enzymology, 65, 499]. DNA sequences of four (4) exons coding for HuIFN-γ and regions before and after the exons were the same as described in Taya et al. [The EMBO J. 1, 953–958 (1980)]. The sequence of the 5'-region including the 1st exon is as follows (same as Table 1):

TABLE 3

| DNA sequence of the 5'-region of HuIFN-γ chromosomal DNA | | | | | |
|---|---|---|---|---|---|
| AGCAAATGAT | CAATGTGCTT | TGTGAATGAA | GAGTCAACAT | TTTACCAGGG | 50 |
| CGAAGTGGGG | AGGTACAAAA | AAATTTCCAG | TCCTTGAATG | GTGTGAAGTA | 100 |
| AAAGTGCCTC | AAAGAATCCC | ACCAGAATGG | CACAGGTGGG | CATAATGGGT | 150 |
| CTGTCTCATC | GTCAAAGGAC | CCAAGGAGTC | TAAAGGAAAC | TCTAACTACA | 200 |
| ACACCCAAAT | GCCACAAAAC | CTTAGTTATT | AATACAAACT | ATCATCCCTG | 250 |
| CCTATCTGTC | ACCATCTCAT | CTTAAAAAAC | TTGTGAAAAT | ACGTAAT<u>CCT</u> | 300 |
| <u>CAGG</u>AGACTT | CAATTAG<u>GTA</u> | <u>TAAATA</u>CCAG | CAGCCAGAGG | AGGTGCAGCA | 350 |
| | | | | →  | |
| <u>MstII</u> | | TATA box | | 1st exon | |
| CATTGTTCTG | ATCATCTGAA | GATCAGCTAT | TAGAAGAGAA | AGATCAGTTA | 400 |
| AGTCCTTTGG | ACCTGATCAG | CTTGATACAA | GAACTACTGA | TTTCAACTTC | 450 |
| <u>BclI</u> | | | | | |
| TTTGGCTTAA | TTCTCTCGGA | AACGATGAAA | TATACAAGTT | ATATCTTGGC | 500 |
| | → | | | | |
| | Protein synthesis | | | | |
| TTTTCAGCTC | TGCATCGTTT | TGGGTTVTVT | TGGCTGTTAC | TGCCAGGACC | 550 |
| CATATGTAAA | AGAAGCAGAA | AACCTTAAGA | AATATTTTGT | AAGTATGACT | 600 |
| TTTTAATAGT | ACTTGTTTGT | GGTTGAAAAT | GACTGAATAT | CGACTTGCTG | 650 |
| TAGCATCTCT | GATAGGCTGT | CATCTCTTGT | AGGCAGTCAT | TTTGAGATTT | 700 |

Table 3 shows that there are a MstII restriction site at 298, TATA box at 319–326 and origin of first exon at 347 from which mRNA is transcribed.

EXAMPLE 4

Preparation of pSVeSmaIγ

Figure 4A:
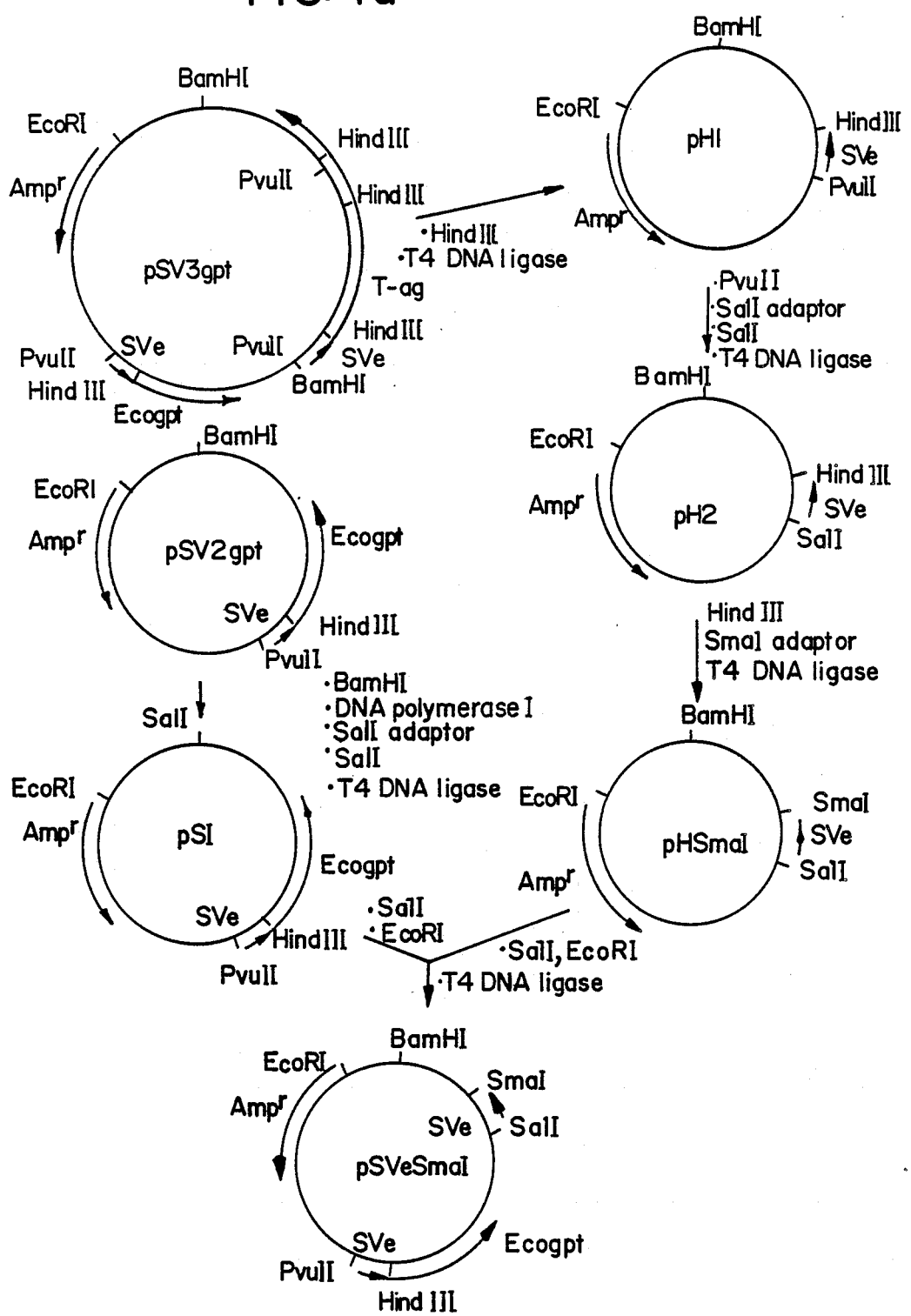
FIGS. 4(a) and 4(b) are schematic representation of the construction of an expression vector, pSVeSmaIγ, having TATA box of HuIFN-γ.
Figure 4B:
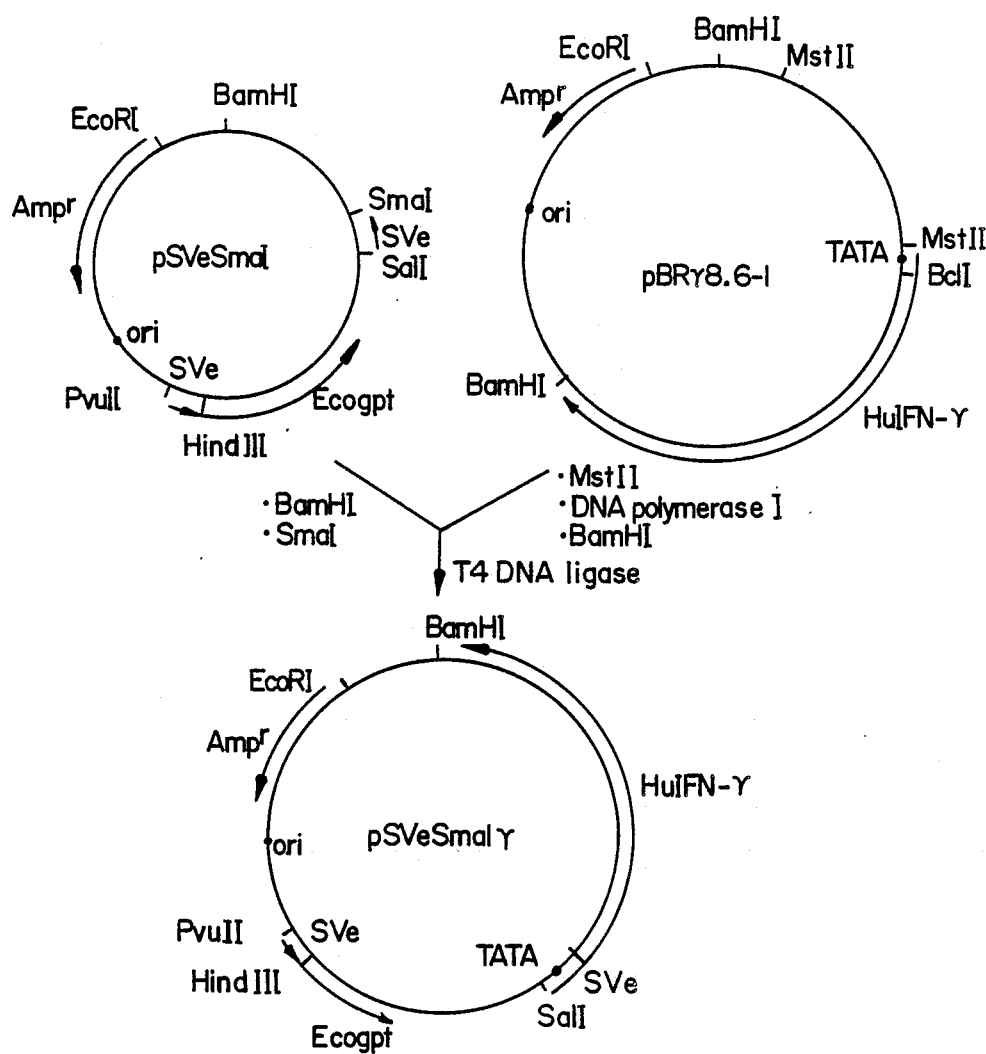

Plasmid pSVeSmaIγ which has the sequence of SV40 promoter region to which chromosomal DNA sequence having TATA box is ligated, is prepared according to the procedures shown in FIGS. 4-(*a*) and 4-(*b*), with the use of pBR8.6-1, pSV2gpt and pSV3gpt [Mulligan, R. C. and P. Berg (1980): Science, 209, 1422] as starting materials.

First, pSV3gpt was digested with HindIII, and the largest DNA fragment was made cyclic with T4 DNA ligase to make pH1. Next, the PvuII site of pH1 was changed into SalI site with the use of SalI linker to make pH2. Next, SmaI site (CCCGGG) was introduced at the HindIII site by using HindIII-SmaI adaptor (AGCTCCCGGG) to make pHSmaI.

pSV2gpt was digested with BamHI, and filled at the termini to make blunt ends with DNA polymerase I (Klenow fragment) and a SalI site was introduced with the use of SalI linker (GGTCGACC) and T4 DNA ligase to make pSI. The pSI was digested with SalI and EcoRI, and ampicillin-resistant gene-bearing DNA fragment was ligated to SalI-EcoRI fragment of pHSmaI having SV40 promoter region to make pSVeSmaI. Next, pBRγ8.6-1 was digested with MstII, and, after the termini were made blunt with DNA polymerase (Klenow fragment), was digested with BamHI to obtain HuIFN-γ sequence-bearing DNA fragment. The DNA fragment was introduced into the pSVSmaI which was digested with SmaI and BamHI, to make pSVemaIγ. DNA sequence of the joining region of SV40 promoter and HuIFN-γ chromosomal DNA is shown in Table 4.

TABLE 4

```
                                                              linker
TTTTTATTTA   TGCAGA              GGCTTTTGCA  AAAAGCT|CCC| T
  SV40 TATA          SV40 early promoter                    HuIFN-γ
CAGGAGACTT   CAATTAGGTA  TAAATACCAG  CAGCCAGAGG  AGGTGCAGCA
  MstII                TATA box                              1st exon
CATTGTTCTG   ATCATCTGAA  GATCAGCTAT  TAGAAGAGAA  AGATCAGTTA
AGTCCTTTGG   ACCTGATCAG  CTTGATCAG   CTTGATACAA  GAACTACTGA
                BclI
```

EXAMPLE 5

Construction of pSVeBalIγ which does not have TATA box of IFN-γ chromosomal DNA.

Figure 5A:
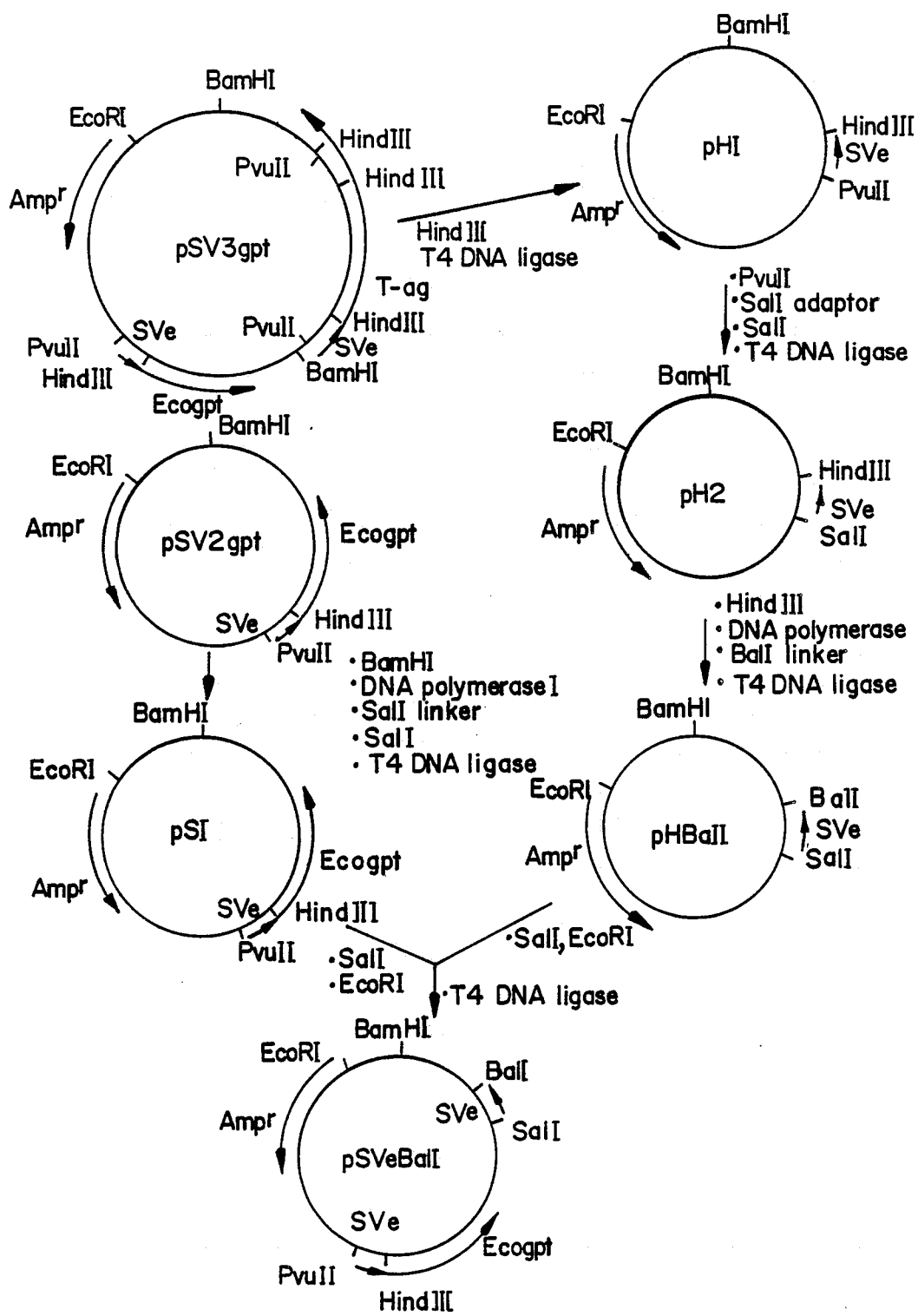
FIGS. 5(a) and 5(b) are schematic representation of the construction of a plasmid pSVeBaIIγ which does not have TATA box of HuIFN-γ chromosomal DNA.
Figure 5B:
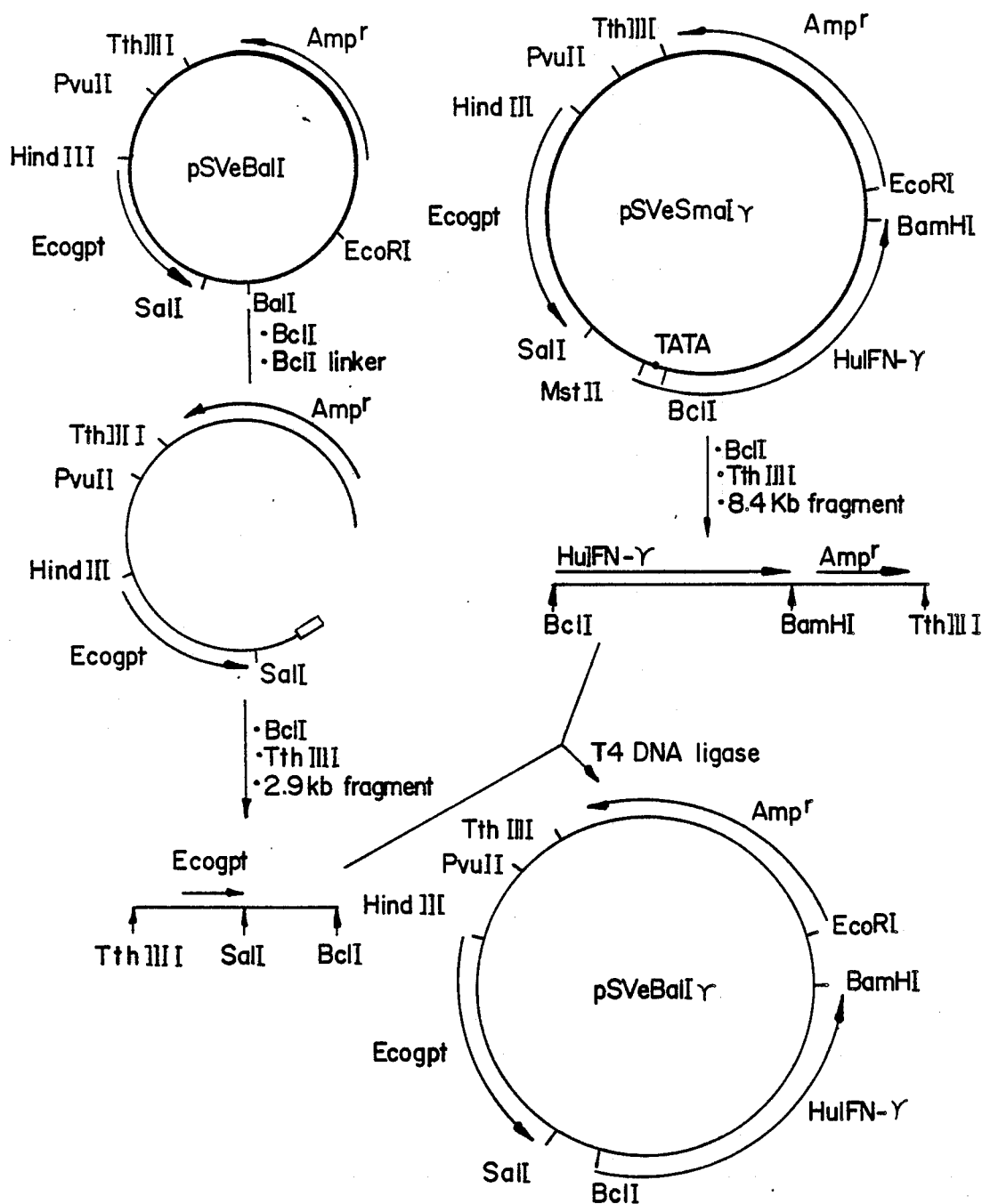

To make pSVeBalI, the same procedure of example 4 was employed as shown in FIG. 5(a) except that BalI site (TGGCCA) was introduced at the HindIII site of pH2. As shown in FIG. 5(b), pSVeBalI was cut with BalI and Bcl linker (CTGATCAG) was ligated to the BalI fragment. Then, the fragment was cut with TthIII I and BclI and BclI-TthIII I 2.9 kb fragment was obtained.

pSVeSmaIγ was cut with BclI and TthIII I and BclI-TthIII I 8.4 kb fragment was obtained.

Then BclI-TthIII I 2.9 kb fragment and BclI-TthIII I fragment were ligated together to make pSVeBalIγ.

As shown in Table 1 (also Table 3), BclI site of HuIFN-γ exist at 414 which is downstream of TATA box at 319-326 and also is in a first exon. So, BclI-TthIII I 8.9 kb fragment does not contain TATA box. DNA sequence of the joining region of SV40 promoter and Human IFN-γ is shown in Table 5.

TABLE 5

```
TTTTTATTTA   TGCAGA                                      GGCTTTTGCA
  SV40 TATA           SV40 early promoter AAAAGCT|TTG GC|TGATCAG  CTTGATACAA  GAACTACTGA  TTTCAACTTC
                                 HuIFN-γ DNA
         linker  BclI
TTTGGCTTAA  TTCTCTCGGA  AACGATGAAA  TATACAAGTT  ATATCTTGGC
                              ─>HuIFN-γ protein
```

EXAMPLE 6

Introduction of pSVeSmaIγ and pSVcBalIγ into animal cell cultures and production of HuIFN-γ

For the purpose of investigating expression of HuIFN-γ genes of pSVeSmaIγ and pSVeBalIγ, the plasmids were introduced into varied animal cell cultures in accordance with procedures of Wigler et al. [Wigler et al. (1977): Cell, 11, 223]. Co-precipitate of plasmid with calcium phosphate was added to cells ($3 \times 10^5$ cells/3.6-ml medium/6-cm round dish) which had been preliminarily grown in Eagle's MEM medium containing 10% fetal calf serum (hereinafter abbreviated as FCS). Cultivation was continued for 48 hours in the medium which was renewed 15 hours after the initiation. IFN activity involved in respective medium was determined. As shown in Tables 6 and 7, production of pSVeSmaIγ which has TATA box of HuIFN-γ was greater than pSVeBalI.

TABLE 6

(each 5 experiments)

| Medium Plasmid | IFN-γ (unit/ml/day) | |
|---|---|---|
| | pSVeSaIγ (with TATA) | pSVeBalIγ (without TATA) |
| 90% MEM 10% FCS | 28–60 | 0–3.5 |

TABLE 7

| | IFN (units/ml) Cell culture | | | | |
|---|---|---|---|---|---|
| Introduced plasmid (7.2 μg/dish) | CHO-K1 (CCL-61) | Hela (CCL-2) | FL (CCL-62) | WISH (CCL-25) | WI-26VA4 (CCL-95.1) |
| pSVeSmaIγ | 64 | 64 | 2 | 1 | 32 |
| pSVeBalIγ | <1 | <1 | <1 | <1 | <1 |

EXAMPLE 7

HuIFN-γ production by CHO-K1 cells transformed with pSVeSmaIγ and pSVeBalIγ

Transformant of CHO-K1 cells of example 6 was selected and was cultivated in a MEM-medium containing 5% FCS, 25 μg/ml mycophenolic acid, 250 μg/ml xanthin. Mycophenolic acid resistant cells were thus selected and HuIFN-γ production was measured.

The results are shown in Table 8.

TABLE 8

| Mycophenolic acid resistant strains (average of each 50 cells) | | |
|---|---|---|
| | IFN-γ (unit/ml/day) | |
| | pSVeSmaIγ | pSVeBalIγ |
| 95% MEM 5% FCS | 5000 | 200 |

(DISCUSSION)

1. Analysis of 5'-region of HuIFN-γ chromosomal DNA As already shown in Table 1 (or 3) we can recognize that:
   (1) CCTCAGG from 298 to 304 is a recognition site of restriction enzyme MstII.
   (2) TATAAATA from 319 to 326 is TATA sequence (TATA box) of HuIFN-γ.
   (3) Messenger RNA is synthesized from AGC at 347 (1st exon).
   4) TGATCAG from 414 to 420 is a recognition site of restriction enzyme BclI.
   (5) HuIFN-γ protein is synthesized from ATG at 475.

2. Analysis of the plasmids

Joining regions of SV40 and HuIFN-γ genomic DNA of the respective plasmids are summarized schematically as follows:

(C) is estimated from the specification of EP No. 159714.

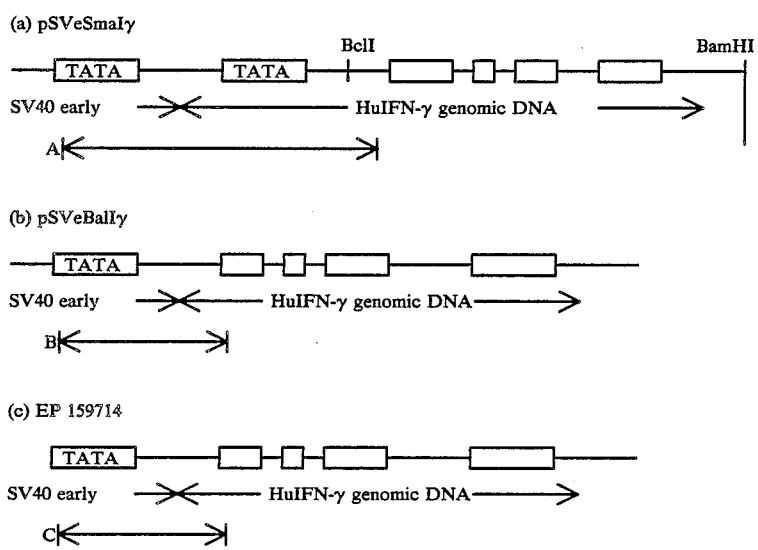

The nucleotide sequences of the joining regions A, B and C of these plasmids are as follows:

```
                                                                    linker
A: TTTTTATTTA    TGCAGA                      GGCTTTTGCA   AAAAGCT|CCC| T
       SV40 TATA            SV40 early promoter                         HuIFN-γ
   CAGGAGACTT   CAATTAGGTA   TAAATACCAG   CAGCCAGAGG   AGGTGCAGCA
   MstII                    TATA box of HuIFN-γ                  1st exon
   CATTGTTCTG   ATCATCTGAA   GATCAGCTAT   TAGAAGAGAA   AGATCAGTTA
   AGTCCTTTGG   ACCTGATCAG   CTTGATCAG    CTTGATACAA   GAACTACTGA
                    BclI B: TTTTTATTTA    TGCAGA                                  GGCTTTTGCA
       SV40 TATA            SV40 early promoter AAAAGCT|TTG GC|TGATCAG    CTTGATACAA   GAACTACTGA   TTTCAACTTC
           linker  BclI       HuIFN-γ DNA
   TTTGGCTTAA   TTCTCTCGGA   AACGATGAAA   TATACAAGTT   ATATCTTGGC
                             ⟶HuIFN-γ protein C: TTTTTATTTA    TGCAGA                                  GGCTTTTGCA
       SV40 TATA            SV40 early promoter
```

-continued

```
AAAAGCT|GATCAG  CTTGATACAA  GAACTACTGA  TTTCAACTTC
      BclI              HuIFN-γ DNA
TTTGGCTTAA  TTCTCTCGGA  AACGATGAAA  TATACAAGTT  ATATCTTGGC
                          →HuIFN-γ protein
```

3. As shown in the above diagram, pSVeSmaIγ has a TATA Box of HuIFN-γ in addition to a TATA box of SV40 early promoter. On the other hand, neither pSVe-BalIγ nor pSVe42 disclosed in EP No. 159714 has a TATA box of HuIFN-γ, and seem to be equivalent in terms of the DNA sequence. Results of measuring productivity show that a plasmid having a TATA box of HuIFN-γ in addition to a TATA box of SV40 early promoter reveals a higher expression than a plasmid not having a TATA box of HuIFN-γ.

4. EP No. 159714 disclosed a high expression of HuIFN-γ. Such high expression is though to be attributable to the use of the enhancer sequence and dhfr gene and TATA box of HuIFN-γ apparently has no role to play in EP No. 159714.

5. Goeddel et al. and Fiers et al. disclose plasmids pSVγ69 and pSV2-IFN-γ, respectively. IFN-γ DNA sequence used in these inventions is cDNA. According to these literature, cDNA was synthesized from mRNA. mRNA of HuIFN-γ is thought to be synthesized from AGC at 347, as mentioned before So, TATA box of HuIFN-γ would not be included in the cDNA sequences of pSVγ69 and pSV2-IFN-γ.

Though the inventors of the present invention did not make a plasmid equivalent to pSVγ69 or pSV2-IFN-γ for direct comparison, it is thought that if these plasmids had had TATA box of HuIFN-γ, it should have revealed a higher expression.

EXAMPLE 8

Figure 6:
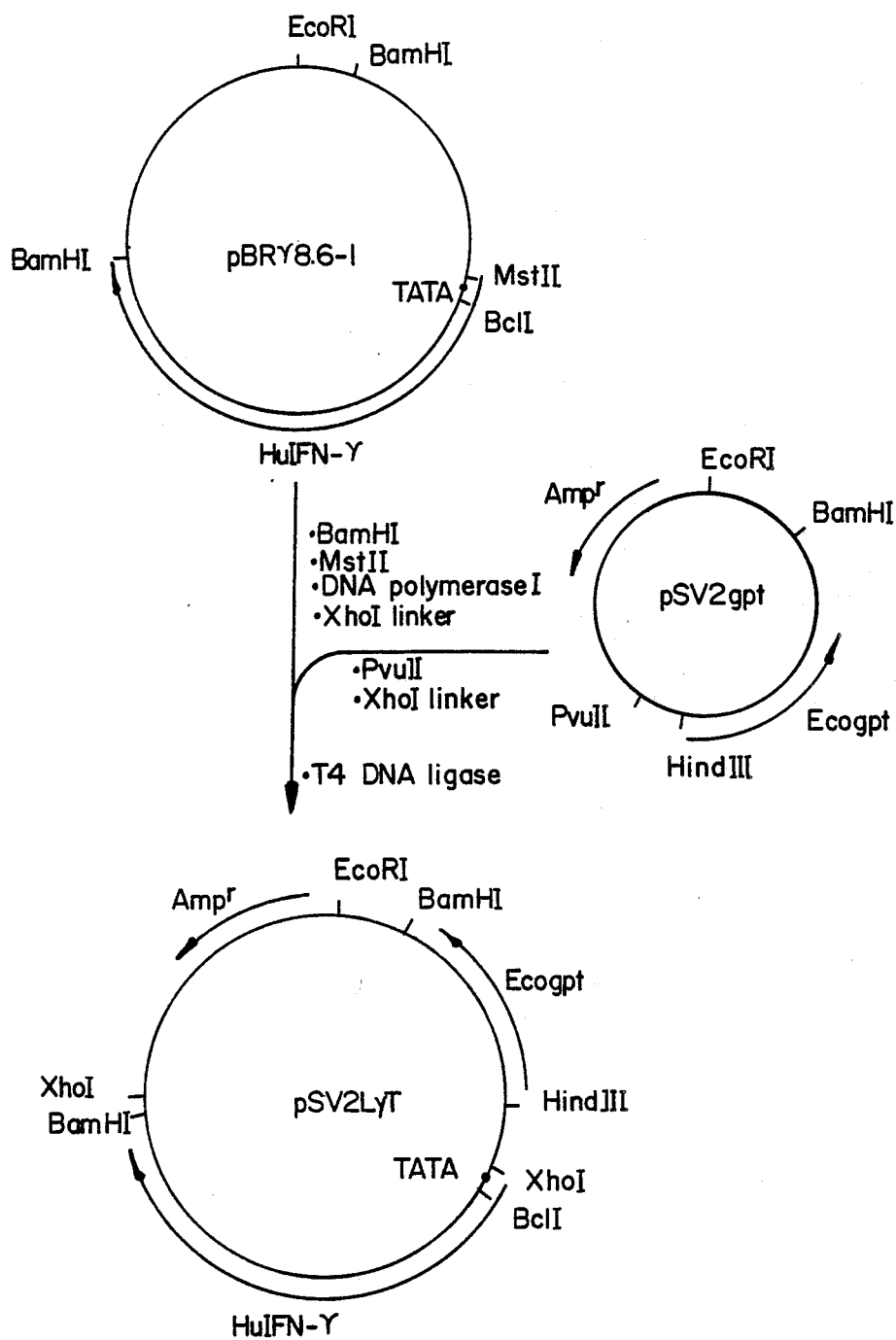
FIGS. 6 and 7 are schematic representation of the constructions of plasmids pSV2LγT and pSV3LγT each of which has a TATA box of HuIFN-γ which is ligated to SV40 late promoter (pSV3LγT has a T-antigen gene while pSV2LγT does not.).

Construction of HuIFN-γ expression vector pSV2LγT, which has a TATA box of HuIFN-γ.

pSV2Lγ T which has a TATA box of HuIFN-γ and whose expression is regulated by SV40 late promoter was constructed as shown in FIG. 6.

pBRγ8.6-1 was cut with BamHI and MstII. The termini were filled with DNA polymerase (Klenow fragment) and were changed into XhoI site by attaching XhoI linker (CCTCGAGG) to the termini. Thus, DNA fragment of about 5.6 kb containing both TATA BOX AND HuIFN-γ chromosomal DNA was obtained.

pSV2gpt was cut with PvuII and PvuII site was changed into XhoI site by using XhoI linker To the XhoI site, the 5.6 kb DNA fragment having XhoI site mentioned above was ligated to make pSV2Lγ T.

EXAMPLE 9

Figure 7:
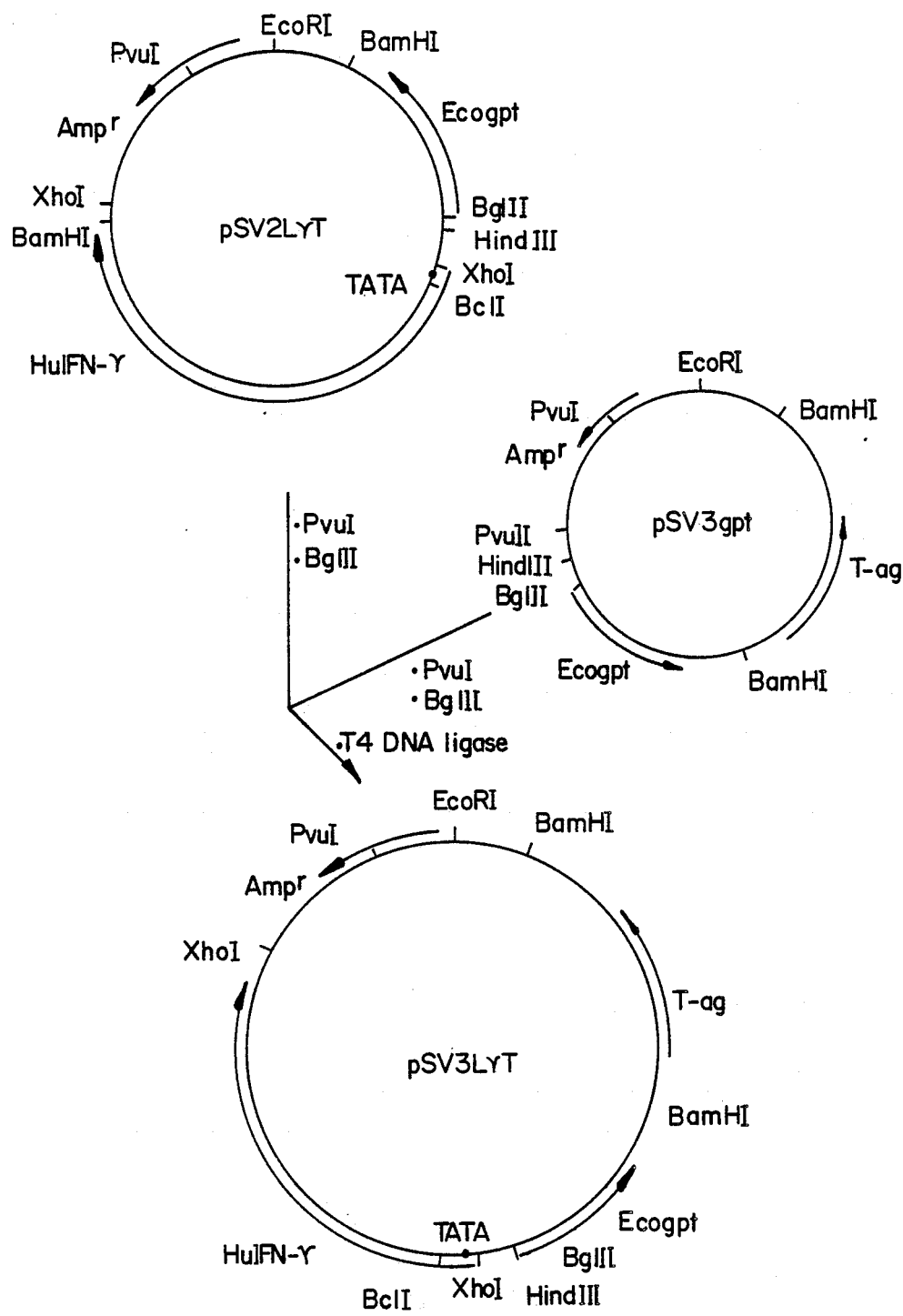

Construction of HuIFN-γ expression vector pSV3LγT which has a TATA box of HuIFN-γ and SV40 T-antigen gene.

pSV3LγT which has a TATA box of HuIFN-γ and SV40 T-antigen and is regulated by SV40 late promoter was constructed as shown in FIG. 7. pSV2LγT was cut with BglII and PvuI, and BglII-PvuI fragment (about 7.8 kb) having HuIFN-γ chromosomal DNA was obtained. This fragment was ligated to a BglII-PvuI large fragment of pSV3gpt to make pSV3Lγ T which contains T-antigen gene of SV40.

EXAMPLE 10

Construction of HuIFN-γ expression vector pSV2Lγ which does not have TATA box.

Figure 8:
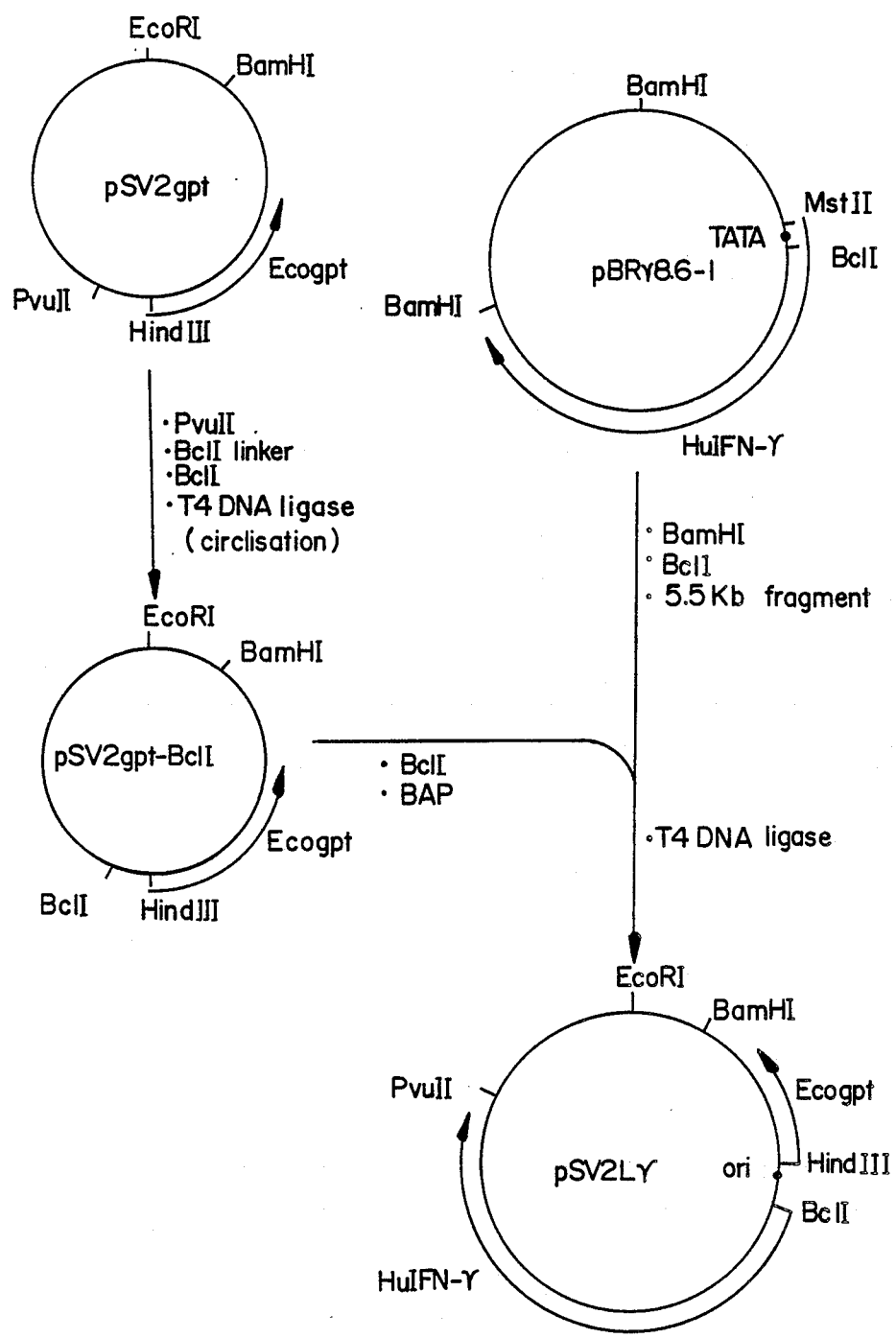
FIG. 8 is a schematic representation of a plasmid pSV2Lγ which does not have a TATA box of HuIFN-γ gene but is ligated to SV40 late promoter.

Procedures for preparing pSV2Lγ are shown in FIG. 8. Plasmid pSV2gpt having both ampicillin-resistant gene and guanine phosphoribosyl transferase gene (Ecogpt) of *Escherichia coli*, was digested with a restriction enzyme PvuII. BclI linker (CTGATCAG) which had been phosphorylated with T4 polynucleotide kinase, was ligated to the termini with the use of T4 ligase, then, after treatment with a restriction enzyme BclI, the DNA fragment was recovered by 0.8% agarose gel electrophoresis. The recovered DNA fragment was circlized with the use of T4 DNA ligase to obtain pSV2gpt-BclI. This plasmid was introduced into *Escherichia coli* GM33 dam− to amplify. The pBR 8.6-1 described in Example 2 was digested with the use of BamHI and BclI. HuIFN-γ gene-bearing DNA fragment of 5.5 kb was recovered, and inserted into the BclI site of pSV2gpt-BclI to obtain pSV2Lγ.

EXAMPLE 11

Expression of HuIFN-γ ligated to SV40 late promoter

HuIFN-γ expression vector pSV2LγT, pSV3LγT or pSV2Lγ was introduced into CHO-K1 cells (ATCC CCL61) according to the method of Wigler et al. [Wigler et al. (1977) cell 11, 233]. Co-precipitate of plasmid-calcium was added to CHO-K1 cells (2×10⁵ cells/3 ml/6 cm diameter well) which were grown in an MEM medium containing 5% FCS. After 15 hours, the medium was renewed and cultured for 48 hours and IFN-γ activity was measured.

Table 9 shows that when pSV2LγT and pSV3LγT which have TATA box of HuIFN-γ and are regulated by SV40 late promoter were introduced into the cells, they revealed high expression of HuIFN-γ compared with pSV2Lγ which does not have TATA box.

This means that transcriptional activity of SV40 late promoter seems to be increased by TATA box. In other word, it is suggested that expression of a protein is increased by using SV40 late promoter in which TATA box is inserted. The fact that pSV3LγT which has T-antigen gene revealed higher expression than pSV2LγT shows that expression of IFN-γ was regulated by SV40 late promoter.

TABLE 9

| Expression efficiency of HuIFN-γ expression vectors | | |
|---|---|---|
| Plasmid introduced 7.2 μg/well | TATA box | IFN-γ produced (units/ml) |
| pSV2LγT | + | 112 |
| pSV3LγT | + | 448 |
| pSV2Lγ | − | 2.8 |

EXAMPLE 12

Production of HuIFN-γ by mycophenolic acid resistant cells

A medium of CHO-K1 cells transfected with pSV2LγT or pSV3Lγ T was as renewed by MEM-medium containing 5% FCS, 25 μg/ml mycophenolic acid, 250 μg/ml xanthin and mycophenolic acid resistant cells were selected. The mycophenolic acid resistant cells were cultured in a 24-well multidish plate confluently, followed by culturing for 24 hours in MEM medium containing 5% FCS, and HuIFN-γ activity was measured. As shown in Table 10, mycophenolic acid resistant cells selected produced HuIFN-γ.

TABLE 10

| Plasmid (7.2 μg/well) | Mycophenolic acid resistant cell | HuIFN-γ (units/ml) |
|---|---|---|
| pSV2LγT | 1-5 | 1,024 |
| | 1-7 | 2,048 |
| | 1-15 | 1,024 |
| | 1-25 | 512 |
| pSV3LγT | 2-5 | 2,048 |
| | 2-7 | 2,048 |
| | 2-16 | 2,048 |

EXAMPLE 13

Production of HuIFN-γ in normal media and serum-free media

The medium of CHO cell into which pSVeSmaγ had been introduced in Example 6, was renewed by MEM medium which contains 10% FCS, 25 μg/ml mycophenolic acid, and 250 μg/ml xanthine. Then, mycophenolic acid-resistant strains were separated therefrom, respectively. Each mycophenolic acid-resistant strain was grown confluently in a 24-well multidish, then cultured for 24 hours with 5% FCS-containing MEM medium, and with FCS-free MEM medium, respectively, and the IFN activities of respective media were determined. Isolated cell lines produced IFN regardless of presence or absence of serum as shown in the following Table 11:

TABLE 11

Production of IFN by pSVeSmaIγ-introduced CHO cells

| | IFN activity (unit/ml/24 hrs) Mycophenolic acid-resistant CHO cell line | | | | |
|---|---|---|---|---|---|
| Medium | CHO-21 | CHO-29 | CHO-46 | CHO-76 | CHO-92 |
| 5% FCS, 95% MEM | 450 | 450 | 117 | 3750 | 234 |
| 100% MEM | 281 | 141 | 281 | 1126 | 70 |

EXAMPLE 14

Purification and properties of HuIFN-γ

Mycophenolic acid-resistant CHO cells, CHO-33, were isolated by the procedures described in Example 13, and cultured in an MEM medium to obtain 120 ml of culture liquid. Then, 1.0 g of Controlled Pore Glass CPG 350 (Electronucleonics Corp.; mesh size 120/200) was added to 60 ml of the obtained culture liquid, and the culture liquid was agitated for 3 fours at 4° C., packed into a column, washed with 150 mM-phosphate-0.15M NaCl buffer (pH 7.4), and eluted by the same buffer which, in addition, contained 50% ethylene glycol. The active fraction was diluted 10-fold with 20 mM phosphate buffer, passed through a 5-ml ConA-Sepharose column to adsorb HuIFN-γ. Then the adsorbed IFN was eluted with 20 mM phosphate buffer containing 0.15M NaCl and 0.15M α-methyl-D-mannoside. The active fractions were collected, dialyzed against 0.2M ammonium acetate (pH 6.0) and 0.15M NaCl, concentrated by polyethylene glycol 20000, and passed through Biogel P-100 (2.6×60 cm) which had been equilibrated with the same buffer to obtain an IFN sample.

The obtained IFN sample lost its activity on treating with acid of pH 2.0 with 0.1% SDS. In testing the sensitivity-promoting effect of the purified IFN on the cytotoxicity of poly I:C, the promoting effect was observed only for human cells. In fact, cells were grown in monolayer on a 24-hole multidish, treated with IFN at 300 units/ml for 20 hours, and then cultured for 24 hours in an MEM medium containing 10 μg/ml poly I:C. While CHO and BHK (hamster cells) underwent no changes, cells of FL, WISH and Hela were observed to become round and exfoliated.

EXAMPLE 15

Selection HuIFN-γ resistant strains

The cell cultures derived from human such as HeLa, FL, WISH, and WI-26 VA-4, were cultured for 24 hours using a 24-well multidish plate in an MEM medium which contained 100 units/ml HuIFN-γ and 5% FCS. After removing the culture liquid, the cultured cells were washed with PBS once, added with MEM buffer containing 10 μg/ml poly I:C, and further cultivated at 37° C. After 16 to 24 hours, it was observed that cells of HeLa, FL and WISH were rounded and exfoliated from the plate bottom, but cells of WI-26 VA-4 were not. This finding suggests that the WI-26 VA-4 are resistant to HuIFN-γ.

EXAMPLE 16

Separation of HuIFN-γ-resistant mutants

FL cells were cultured on the whole bottom surface of 75 cm² of a flask. Then the medium of the culture was renewed by an MEM medium which contained 100 units/ml HuIFN-γ, and 10 vg/ml poly I:C, and incubated for 48-hour. Although most of FL cells were exfoliated from the bottom, the medium was replaced with another MEM medium containing 100 units/ml HuIFN-γ, and the culture was still incubated for about one month. Colonies of HuIFN-γ-resistant FL cells were developed, proliferated, and established.

EXAMPLE 17

Obtainment of transformed cell lines

The pSVeSmaIγ which was prepared so as to express HuIFN-γ in Example 4, or the pSV2gpt which had no HuIFN-γ gene, was introduced into the HuIFN-γ-sensitive HeLa, FL or WISH cells, or the HuIFN-γ-resistant WI-26 VA-4 cells, and the HuIFN-γ-resistant FL cells in accordance to the calcium phosphate method [Wigler et al. (1977): Cell, 11. 223]. Co-precipitate of 1.44 μg plasmid with calcium phosphate was added to the above cells (3×10⁵ cells/3.6 ml medium/6 cm diameter disk) which had been preliminarily grown in an Eagle's MEM medium containing 10% newborn calf serum. After 15 hours, the medium was renewed, and after 48-hour incubation, the medium was again renewed by another medium which contained 25 μg/ml mycophenolic acid, 250 μg/ml xanthine, 1.0 μg/ml aminopterin, 25 μg/ml adenine, and 5 μg/ml thymidine, and after further 2-week incubation, the numbers of developed transformant colonies were counted. As shown in Table 12 below, transformants were obtained from all used strains for pSV2gpt, while few transformant colonies were obtained from HuIFN-γ-sensitive strains for gene-containing pSVeSmaIγ or pSV2pTKγ, although many were from HuIFN-γ-resistant WI-26 VA-4 and HuIFN-γ-resistant FL cells.

TABLE 12

| Plasmid | Numbers of transformant colonies formed | | | | |
|---|---|---|---|---|---|
| | HeLa | FL | WISH | WI-26 VA-4 | HuIFN-γ resistant FL |
| PSV2gpt | 120 | 52 | 28 | 36 | 40 |
| pSVeSmaIγ | 1 | 0 | 3 | 28 | 37 |

EXAMPLE 18

Production of HuIFN-γ by WI-26 VA-4

The colonies of WI-26 VA-4 transformant obtained in Example 17 using pSVeSmaIγ or aSV2pTKγ were separated, and proliferated in an MEM medium containing 5% FCS. The transformant was proliferated on the whole bottom surface of the 24-well multiplate. After the medium was renewed, and the culture was incubated for 24 hours, the IFN activity in the culture liquid was determined. The HuIFN-γ activities of 32.3 units/24 hr/$10^6$ cells were observed for transformants by pSVeSmaIγ. In addition, using 1.44 μg of pSV2γ8.6-1 or pSVeSmaI, WI-26 VA-4 strain was transformed in a similar way to that in Example 17. The obtained results are shown in Table 13.

TABLE 13

| Plasmid | Number of transformed cell IFN-γ activity (Unit/24/ hr/$10^6$ cells) | | | | Total transformed cells |
|---|---|---|---|---|---|
| | 0 | <10 | <$10^2$ | <$10^3$ | |
| pSV2γ8.6-1 | 8 | 1 | 0 | 0 | 9 |
| pSVeSmaIγ | 5 | 1 | 2 | 0 | 8 |

EXAMPLE 19

Expression of IFN by blood cell-derived cell lines

The pSVeSmaIγ described in Example 4 was introduced into blood cell-derived cell lines obtained from ATCC or others according to the method of Oi, et al. [Oi, V. T. et al. (1980): Proc. Natl. Acad. Sci. USA, 80. 825]. Plasmid pSVeSmaIγ-bearing *Escherichia coli* K-12 strain C600 −m− was cultured with an L medium at 37° C. until the absorbance at 600 nm reached 0.6 to 0.8. After the addition of chloramphenicol up to 125 μg/ml and the further culturing for 12 to 16 hours, the bacteria were centrifuged and collected. Then, cold 0.05M tris HCl (pH 8.0) which contained sucrose by 20% per 250 ml medium, was added to disperse the bacteria After the addition of 0.25 ml of 5 mg/ml lysozyme solution, and 5-minute standing on ice, 0.5 ml of 0.25M EDTA (pH 8.0) was added, and the liquid was allowed to stand again for 5 minutes on ice. Then after 0.5 ml of 0.05M Tris.HCl (pH 8.0) was added again, the liquid was incubated for 10 to 15 minutes at 37° C. to protoplastize the bacteria. The protoplast was diluted with 10 ml of DMEM medium containing 10% sucrose, and allowed to stand for 10 minutes at room temperature. The cells were cultured in DMEM medium containing 10% FCS to $10^6$ cells/ml, and centrifuged at about 500×g at room temperature. After removing the supernatant, the precipitate was added to by 2 ml of 50% polyethylene glycol solution (pH 8.0) in DMEM medium, gently stirred, and centrifuged for 3 minutes at 500×g. The cells were washed with 7 ml of DMEM medium, dispersed into DMEM medium containing 10% FCS, and cultured at a cell concentration of 2×$10^5$ cells/well ml with a 24-well multidish plate. After a 24-hour cultivation, the culture supernatant was taken, and its IFN activity was determined. As shown in Table 14 below, pSVeSmaIγ-introduced cells exhibited IFN activities.

TABLE 14

| Production of HuIFN-γ by blood cell-derived cell lines | |
|---|---|
| | IFN activity (units/ml/48 hrs) |
| MOPC-31C (CCL-130) | 160 |
| MPC 11 (CCL-167) | 30 |
| MB III (CCL-32) | 3 |
| BRL-1 (CRL-1378) | 3 |
| RPMI7666 (CCL-114) | 3 |
| MOLT-3 (CRL-1552) | 3 |
| L1210 (CCL-219) | 60 |
| CCRF-CEM (CCL119) | 12 |
| *EL-4 | 60 |
| U937 (CRL-1593) | 12 |
| X63-Ag8 (CRL-1580) | 60 |

*EL-4: Farrar, J. J. et al.: (1980) J. Imm. 125, 2555.

EXAMPLE 20

Production of HuIFN-γ with normal media and serum-free media

The medium of MOPC-31C cells into which PSVeSmaIγ had been introduced by the protoplast fusion method in Example 19, was renewed by a DMEM medium which contained 10% FCS, 25 μg/ml mycophenolic acid, 250 μg/ml xanthine, 5 μg/ml thymidine, 0.1 μg/ml aminopterin, and 25 μg/ml adenine, and the cells were further cultured for 3 to 4 weeks, and mycophenolic acid-resistant cell colonies were isolated therefrom. Each of the mycophenolic acid-resistant cells was cultured on the whole bottom surface of a 24-well multidish, and further cultured with 5% FCS-containing or FCS-free DMEM medium for 48 hours, and the IFN activity in the medium was determined. As shown below, the isolated cell lines proved to produce HuIFN-γ regardless of the presence or absence of serum. Similarly, both MPC 11 and EL4 transformed lines produced IFN.

TABLE 15

| Production of HuIFN-γ by isolated mycophenolic resistant cell lines | | | |
|---|---|---|---|
| | IFN activity (units/ml/48 hrs) Origin of mycophenolic acid resistant strain | | |
| Medium | MOPC-31C | MPC11 | EL4 |
| 5% FCS, 95% DMEM | | | |
| 100% DMEM | 200 | ND* | ND* |

*ND: Not tested.

What we claim:

1. A plasmid which comprises:
   (a) a chromosomal DNA sequence coding for human interferon-γ (HuIFN-γ) having its TATA box; and
   (b) and SV40 early promoter having its TATA box, and in which said sequence (a) is ligated to the TATA box of said SV40 early promoter.

2. The plasmid according to claim 1 which is PSVeS-maIγ.

3. Animal cells in culture transformed with a plasmid which comprises:
(a) a chromosomal DNA sequence coding for human interferon-γ (HuIFN-γ) having its TATA box and
(b) and SV40 early promoter having its TATA box; and in which said sequence (a) is ligated to the TATA box of said SV40 early promoter.

4. The animal cells according to claim 3 wherein said cell line is selected from the group consisting of CHO-K1, HeLa, WI-26 VA-4, MOPC-31, EL-4, MB, RPMI7666, MOLT-3, BRL-1 and L1210.

* * * * *

UNITED STATES PATENT AND TRADEMARK OFFICE
CERTIFICATE OF CORRECTION

PATENT NO.  : 4,970,161

DATED       : November 13, 1990

INVENTOR(S) : Tetsu KAKUTANI et al.

It is certified that error appears in the above-identified patent and that said Letters Patent is hereby corrected as shown below:

On the title page, Item [30], "59-11648" should read --59-119648--.

Signed and Sealed this

Seventh Day of April, 1992

Attest:

HARRY F. MANBECK, JR.

*Attesting Officer*    *Commissioner of Patents and Trademarks*